United States Patent
Endo et al.

(10) Patent No.: US 9,820,645 B2
(45) Date of Patent: Nov. 21, 2017

(54) OPHTHALMOLOGIC APPARATUS

(71) Applicant: NIDEK CO., LTD., Gamagori, Aichi (JP)

(72) Inventors: Masakazu Endo, Okazaki (JP);
Masaaki Hanebuchi, Nukata (JP);
Yasuhiro Furuuchi, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 51 days.

(21) Appl. No.: 14/813,846

(22) Filed: Jul. 30, 2015

(65) Prior Publication Data

US 2016/0038023 A1 Feb. 11, 2016

(30) Foreign Application Priority Data

Jul. 31, 2014 (JP) .................. 2014-157182

(51) Int. Cl.
*A61B 3/10* (2006.01)
*G01B 9/02* (2006.01)
*A61B 3/00* (2006.01)

(52) U.S. Cl.
CPC .............. *A61B 3/1005* (2013.01); *A61B 3/00* (2013.01); *A61B 3/0025* (2013.01); *A61B 3/10* (2013.01); *A61B 3/102* (2013.01); *G01B 9/02083* (2013.01); *G01B 9/02091* (2013.01)

(58) Field of Classification Search
CPC ........... A61B 3/00; A61B 3/0025; A61B 3/10; A61B 3/1005; A61B 3/102; G01L 39/02083; G01L 39/02091
USPC ................. 351/200, 205, 206, 208
See application file for complete search history.

(56) References Cited

U.S. PATENT DOCUMENTS

| | | | | |
|---|---|---|---|---|
| 8,348,427 B2* | 1/2013 | Buckland | ............... | A61B 3/102 351/206 |
| 8,928,890 B2* | 1/2015 | Nebosis | ............... | A61B 5/0066 356/497 |
| 8,939,582 B1* | 1/2015 | Spaide | ............... | G01B 9/02091 351/205 |
| 8,985,770 B2* | 3/2015 | Ono | ....................... | A61B 3/102 351/200 |
| 9,068,812 B2* | 6/2015 | Sato | ....................... | A61B 3/102 |
| 9,149,180 B2* | 10/2015 | Muto | ..................... | A61B 3/102 |
| 9,310,186 B2* | 4/2016 | Abdulhalim | ....... | G01B 9/02004 |

(Continued)

FOREIGN PATENT DOCUMENTS

JP 2012-075641 A 4/2012

*Primary Examiner* — William R Alexander
(74) *Attorney, Agent, or Firm* — Oliff PLC

(57) ABSTRACT

The present invention relates to an ophthalmologic apparatus for acquiring depth information of an eye including a light source; a measurement optical path guiding measurement light; a reference optical path generating reference light; and a detector generating a detection signal containing an interference signal of the measurement light via the measurement optical path and the reference light coming from the reference optical path; an actuator driving at least part of the interference optical system to vary an optical path length difference between the measurement optical path and the reference optical path; a standard optical system including optical members disposed corresponding to the optical path length differences in one of the measurement optical path and the reference optical path. Optical members guide part of the measurement light or the reference light to the detector.

11 Claims, 5 Drawing Sheets

(56) References Cited

U.S. PATENT DOCUMENTS

| | | | |
|---|---|---|---|
| 9,596,987 B2* | 3/2017 | Fujino | A61B 3/1005 |
| 2009/0027685 A1* | 1/2009 | Abe | A61B 3/102 |
| | | | 356/477 |
| 2009/0153876 A1* | 6/2009 | Chan | A61B 3/102 |
| | | | 356/521 |
| 2010/0181462 A1* | 7/2010 | Sugita | G01B 9/02044 |
| | | | 250/201.8 |
| 2011/0205548 A1* | 8/2011 | Sugita | A61B 3/102 |
| | | | 356/496 |

* cited by examiner

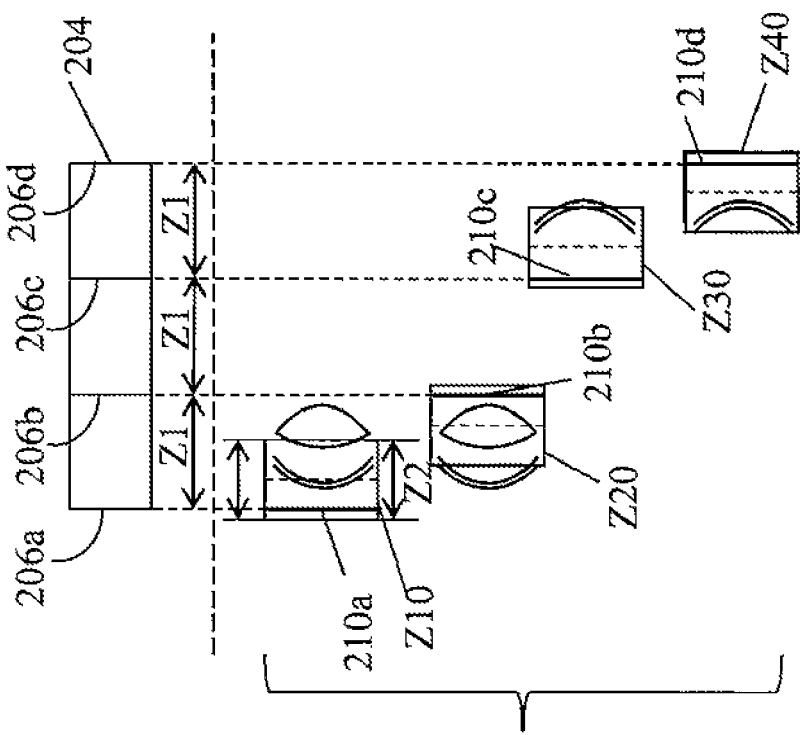
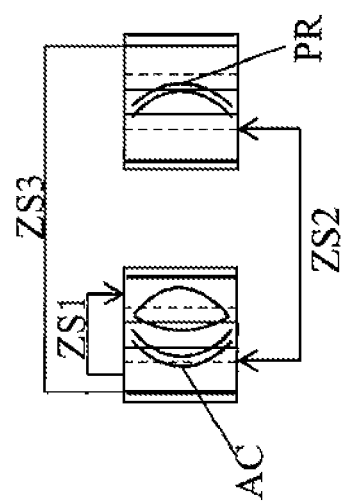
FIG.5

OPHTHALMOLOGIC APPARATUS

CROSS REFERENCE TO RELATED APPLICATION

This application is based upon and claims the benefit of priority of Japanese Patent Application No. 2014-157182 filed on Jul. 31, 2014, the contents of which are incorporated herein by reference in its entirety.

BACKGROUND OF THE INVENTION

The present invention relates to an ophthalmologic apparatus for acquiring depth information for an eye Fourier-domain OCT (optical coherence tomography), which can be acquired more quickly than an A-scan waveform than time-domain OCT, is currently a mainstream apparatus for acquiring tomographic images of tissue (e.g., anterior chamber or fundus) for an eye (refer to JP-A-2012-75641, for example).

SUMMARY

In general Fourier-domain OCT apparatus, the imaging range in the depth direction is restricted to a portion of the anterior chamber or a fundus region. Although Fourier-domain OCT apparatus have been proposed that have a variable wavelength light source whose coherence length is set longer to image the entire eye at one time, they are complex in configuration and expensive.

A technical object of the present invention is to provide an ophthalmologic apparatus capable of solving at least one of the problems of the prior art.

To attain the above object, the invention provides the following configurations:

An ophthalmologic apparatus comprising:
an interference optical system including:
a light source to emit light;
a measurement optical path configured to guide, to an eye, measurement light which is generated based on the light emitted from the light source;
a reference optical path configured to generate reference light which is generated based on the light emitted from the light source; and
a detector configured to generate a detection signal containing an interference signal of the measurement light guided to the eye via the measurement optical path and the reference light coming from the reference optical path;
an actuator configured to drive at least part of the interference optical system to vary an optical path length difference between the measurement optical path and the reference optical path;
a standard optical system including a plurality of optical members disposed corresponding to the optical path length differences produced by driving the actuator in one of the measurement optical path and the reference optical path, the plurality of optical members being configured to guide part of the measurement light or the reference light to the detector; and
a processor configured to:
acquire first depth information including a first interference signal of the measurement light coming from a first part of the eye and the reference light by processing the detection signal received from the detector where the optical path length difference is a first value;
acquire second depth information including a second interference signal of the measurement light coming from the second part of the eye and the reference light by processing the detection signal received from the detector where the optical path length difference is a second value different from the first value,
set a positional relationship between the first depth information and the second depth information based on standard interference signal which is an interference signal of the lights coming from the optical members.

BRIEF DESCRIPTION OF THE DRAWINGS

FIG. 5 shows an example manner of combining pieces of depth information together in the ophthalmologic apparatus according to the second specific embodiment.

DESCRIPTION OF ILLUSTRATIVE EMBODIMENTS

A typical, basic embodiment of the present invention will be described below with reference to the drawings.

An ophthalmologic apparatus 1 according to a basic embodiment will be outlined below. Although the basic embodiment will be directed to a case that the ophthalmologic apparatus 1 is an OCT apparatus, the invention is not limited to such a case and can broadly be applied to ophthalmologic apparatus having an interference optical system such as eye dimensions measuring apparatus.

Figure 1:
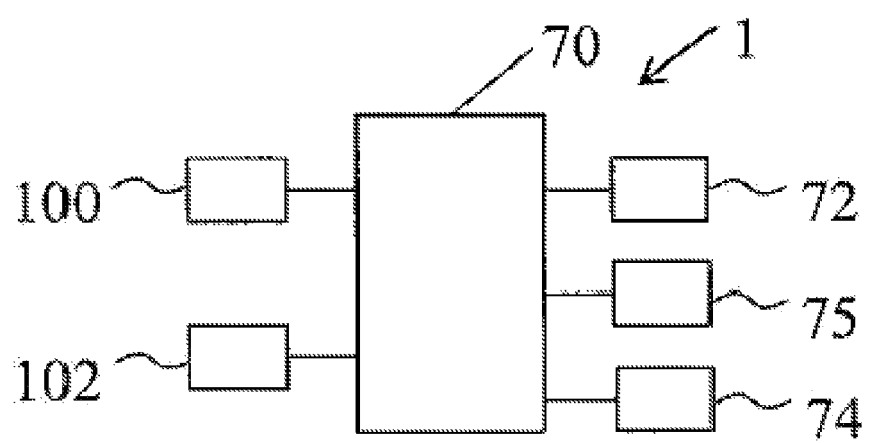
FIG. 1 is a block diagram of a control system of an ophthalmologic apparatus according to the embodiment.
Figure 2:
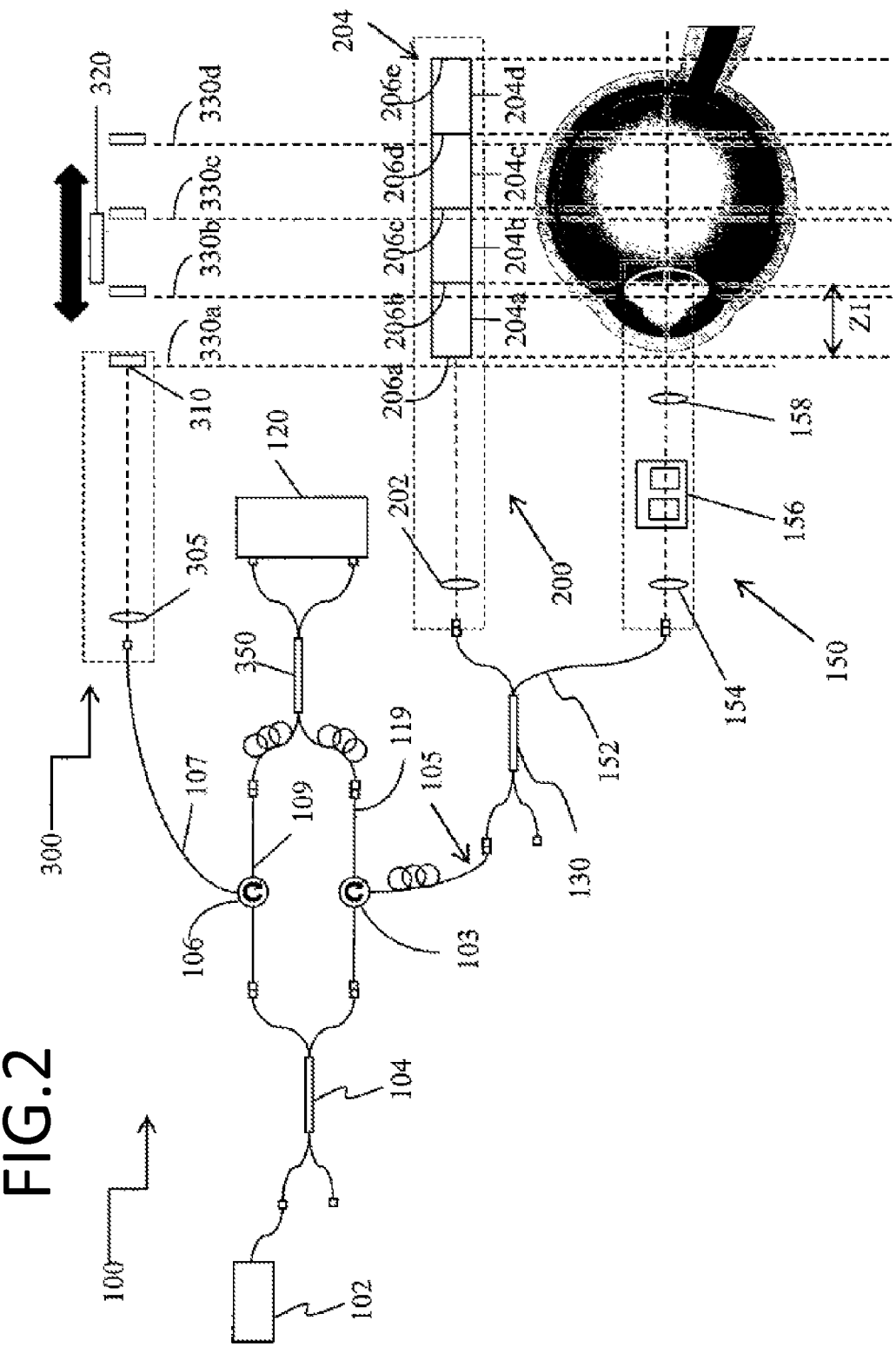
FIG. 2 shows an optical configuration of an ophthalmologic apparatus according to a first specific embodiment.
Figure 4:
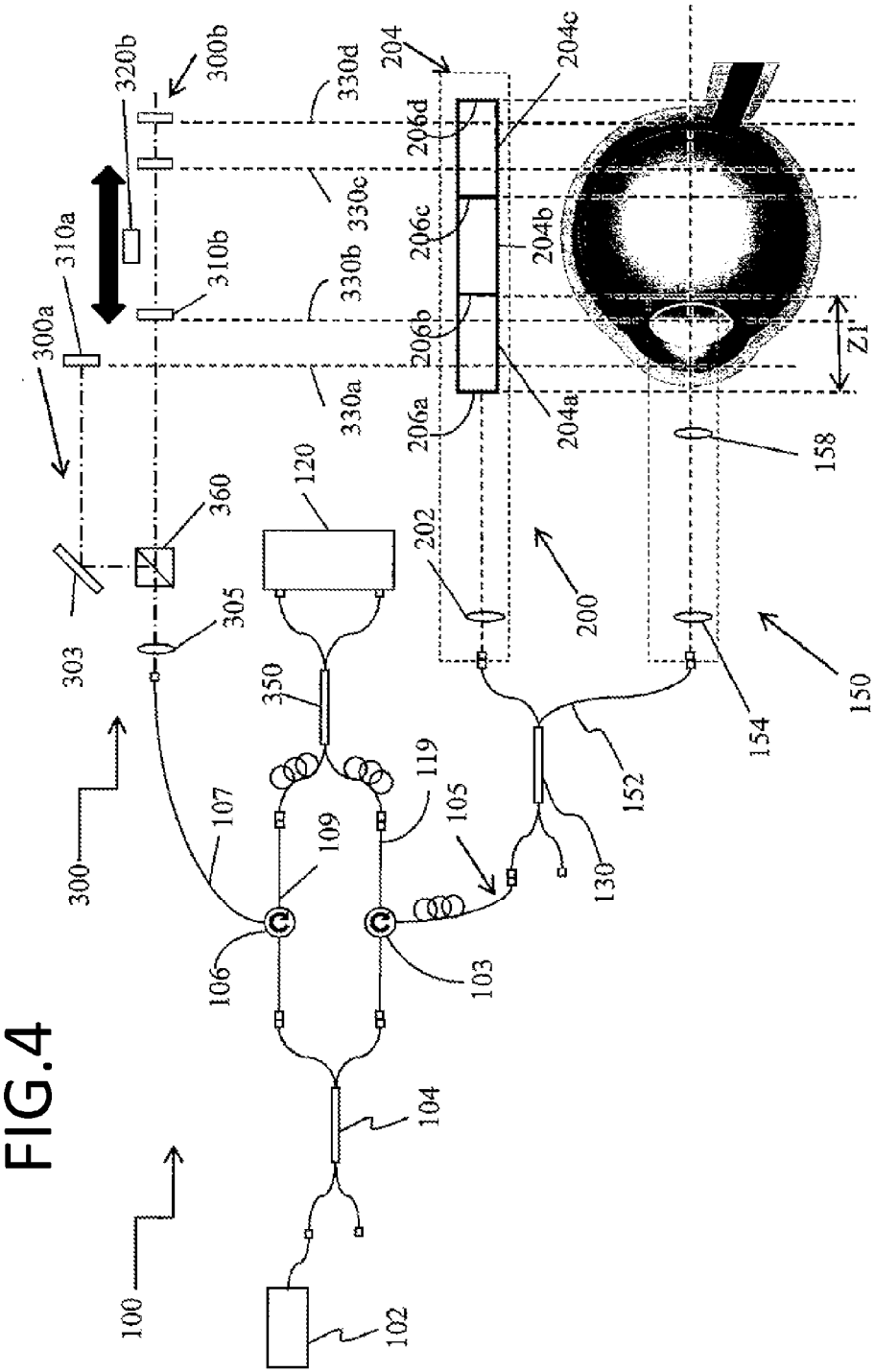
FIG. 4 shows an optical configuration of an ophthalmologic apparatus according to a second specific embodiment.

The ophthalmologic apparatus 1 has, as main optical systems, an interference optical system 100 and a standard optical system 200 (see FIGS. 1, 2, and 4). For example, the ophthalmologic apparatus 1 sets positional relationships between a plurality of pieces of depth information acquired with different optical path length differences, using, as references, standard interference signals generated by the interference optical system 100 and the standard optical system 200.

<Fundamental Configuration>

The ophthalmologic apparatus 1 is based on Fourier-domain optical coherence tomography (FD-OCT), for example, and includes the interference optical system (OCT optical system) 100 and a computation control device (e.g., control unit 70). Typical examples of FD-OCT are swept source OCT (SS-OCT) and spectral domain OCT (SD-OCT). As a further alternative, time-domain OCT (TD-OCT) may be employed.

The interference optical system 100 may have an interferometer configuration for acquiring depth information of an eye E to be examined based on the principle of OCT. More specifically, the interference optical system 100 may be such as to have a light source 102, a splitter (optical splitter), a measurement optical path, a reference optical path, a combiner (optical combiner), and a photodetector (e.g., detector 120). In this case, the splitter (e.g., coupler 104) splits light coming from the light source 102 into light beams to travel along the measurement optical path and the reference optical path, respectively. A beam splitter, a halfmirror, a fiber coupler, a circulator, or the like is used as each of the splitter and the combiner.

The measurement optical path has a structure (e.g., guide optical system 150) for guiding light to the eye E. The reference optical path has a structure (e.g., reference optical system 300) for causing light to travel in the apparatus 1 so as to interfere with measurement light. The reference optical path is used for generating reference light. The combiner combines (causes interference between) measurement light that comes from the measurement optical path after being reflected by the eye E and reference light coming from the reference optical path. The photodetector (e.g., detector 120) detects a spectrum signal that contains an interference signal of measurement light that has been introduced to the eye E via the measurement optical path and reference light coming from the reference optical path.

The computation control device (e.g., control unit 70) may be such as to perform processing of controlling the individual units of the apparatus 1, image processing, computation, etc. More specifically, the computation control device may acquire and process a spectrum signal containing interference signals at respective wavelengths and may further produce data in the depth direction (i.e., depth information) of the eye E by processing the spectrum signal.

The measurement optical path may be provided with a scanning unit (e.g., optical scanner 156) for performing a scan with measurement light. The computation control device may produce tomographic images of the eye E by arranging pieces of depth information acquired at respective scanning positions. The computation control device may store or display processing results in a storage unit (e.g., memory 72) or on a display unit (e.g., display unit 75).

<Optical Path Length Difference Varying Unit>

The ophthalmologic apparatus 1 may be equipped with an optical path length difference varying unit for varying the optical path length difference between the measurement optical path and the reference optical path. More specifically, the optical path length difference varying unit may be equipped with a drive unit (actuator) for moving at least part of the interference optical system 100 to vary the optical path length difference between the measurement optical path and the reference optical path. The drive unit (e.g., drive unit 320 or 320*b*) may move either an optical member (e.g., optical member 310 or 310*b*) disposed in the measurement optical path or the reference optical path or the entire interference optical system 100. For example, the drive unit is drive-controlled by the computation control device. The optical path length difference varying unit varies the optical path length difference by, for example, varying at least one of the optical path length of measurement light and that of reference light. The following description will be made with an assumption that the optical path length difference is one between the measurement optical path and the reference optical path unless otherwise specified.

Alternatively, to adjust the optical path length difference, the optical path length difference varying unit may move at least part of the optical member 310 disposed in the interference optical system 100 in the optical axis direction. The optical path length of measurement light is varied by, for example, moving, in the optical axis direction, an optical member (e.g., an end portion of an optical fiber) disposed in the measurement optical path.

The computation control device may acquire a plurality of pieces of depth information with different optical path length differences by varying the optical path length difference by controlling the optical path length difference varying unit.

That is, in this case, pieces of depth information are acquired with different optical path length differences by varying the optical path of measurement light or reference light. In other words, pieces of depth information are acquired using measurement light beams or reference light beams having different optical path lengths. The computation control device may acquire pieces of depth information with preset optical path length differences by varying the optical path length difference by moving the optical member to a plurality of preset positions. The optical path length difference may be varied by a manual manipulation of an operator.

<Standard Optical System>

The standard optical system 200 may be provided to generate a standard interference signal to be used for setting positional relationships between a plurality of pieces of depth information. The standard optical system 200 may be equipped with standard portions (e.g., reflection portions 206*a*-206*e*) for guiding part of measurement light or reference light to the detector. More specifically, the standard portions may be optical members. The standard portions may be used as a scale. The standard portions may be disposed in one of the measurement optical path and the reference optical path. A plurality of standard portions may be provided so as to correspond to respective optical path length differences produced by the optical path length difference varying unit. The standard portions may be disposed at prescribed positions in one of the measurement optical path and the reference optical path. The standard portions may be equipped with structures for guiding part of measurement light or reference light to the detector by reflecting or transmitting it and may thus be provided as a standard reflection optical system or a standard transmission optical system.

The standard optical system 200 may be provided as an optical system for generating, using light coming from the light source, standard light beams to serve as standards for setting of positional relationships between a plurality of pieces of depth information with different optical path length differences.

Where the optical path length of one of the measurement optical path and the reference optical path is varied by the optical path length difference varying unit, the standard optical system 200 may be disposed in the other of the measurement optical path and the reference optical path.

As for the specific configuration of each standard portion, it may be a light transmission member (e.g., glass member or plastic member) capable of reflecting part of incident light or a light reflection member (e.g., cellophane member or filter) capable of transmitting part of the incident light. The standard optical system 200 may be an optical fiber. In this case, the standard portions are formed by forming defective portions in the optical fiber at prescribed positions.

The reflectivity of a reflection surface formed in each standard portion may be set by AR coating. A configuration is possible in which reflection surfaces (e.g., polished surface or sand-blasted surface) have different reflectivity and each reflection surface corresponds to a reflection peak which is determined by checking its SNR. Another configuration is possible in which reflection surfaces are formed so as to produce different numbers of reflection peaks (e.g., the number of cellophane layers is varied) and each reflection surface corresponds to a set of reflection peaks which is determined by checking the number of reflection peaks. The reflection surface an interference signal corresponds to may be determined according to its phase or variance.

The standard optical system 200 may be such that plurality of reflective optical members having different lengths are provided and the reflection optical member to be disposed in the standard optical system 200 is switched depending on the change in an optical path length. In this case, an actuator for the switching may be provided. The lengths of the reflection optical members are set according to respective switching result optical path lengths of reference light (or measurement light). The reflection optical members may be flat-plate-like optical members such as glass plates, and a plurality of optical members may be disposed at different positions and switching may be made between them depending on the change in the optical path length.

Where a plurality of standard portions are arranged at different positions in the optical axis direction, the standard optical system 200 may be provided with a focus adjusting unit for securing proper light coming from each standard portion. For example, a focusing optical member (e.g., (focusing lens) is disposed in the optical path of the standard optical system 200. The focus position in the standard optical system 200 may be adjusted by moving the focusing optical member. In this case, the focus position may be adjusted according to a switching result optical path length of reference light (or measurement light). Proper light coming from each standard portion may be secured by adjusting the focus position so that focusing is made on the standard portion corresponding to a switching result optical path length of reference light (or measurement light).

When the optical path length difference is varied, the depth information acquisition region may change. In view of this, a focus position varying unit for varying the focus position of measurement light in the depth direction of the eye E may be disposed in the measurement optical path (e.g., guide optical system 150). The focus position varying unit may be implemented by various methods such as moving an objective lens system in the optical axis direction, inserting/removing a lens, and electrically varying refraction power using a liquid crystal lens.

Where the anterior chamber and the fundus are measured separately, the standard optical system 200 may be detached from the measurement optical path. For example, the standard optical system 200 is detached from the measurement optical path by disposing a light shield member in the optical path of the standard optical system 200.

<Setting Using Standard Interference Signals>

Figure 3:
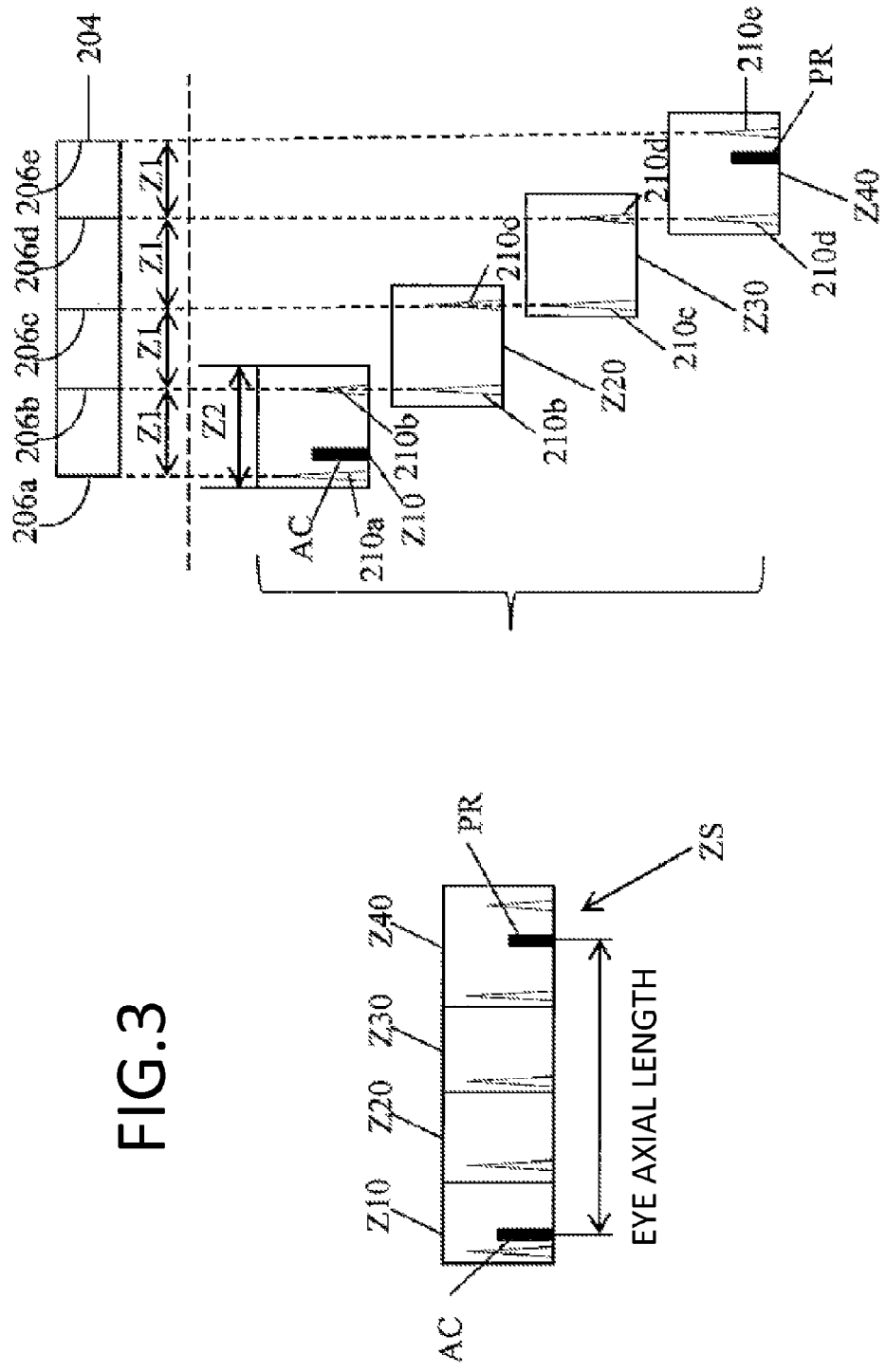
FIG. 3 shows an example method of synthesizing depth information together in the ophthalmologic apparatus according to the first specific embodiment.

The computation control device may set a positional relationship between first depth information and second depth information using standard interference signals (e.g., interference signal 210a) that are generated by the standard optical system 200 (see FIG. 3). For example, the standard interference signals are interference signals of light coming from a standard portion(s). For example, the first depth information and the second depth information are acquired with different optical path length differences between the measurement optical path and the reference optical path. That is, the computation control device may set, using standard interference signals, a positional relationship between a plurality of pieces of depth information acquired with different optical path length differences.

As for the setting of a positional relationship, the computation control device may use standard interference signals for a positional relationship adjustment in combining the first depth information and the second depth information with each other. The computation control device may set a positional relationship between the first depth information and the second depth information.

The first depth information may contain a first interference signal of reference light and measurement light coming from a first part (e.g., cornea) of the eye E. The second depth information may be acquired with a different optical path length difference than the first depth information is, and contain a second interference signal of measurement light coming from a second part of the eye E and reference light.

The computation control device may detect positions of the first part (e.g., cornea) and the second part (e.g., retina) based on the first depth information and the second depth information, respectively. The computation control device may determine a distance between the first part and the second part based on their detected positions and the positional relationship that has been set in the above-described manner. Examples of the distance between the first part and the second part are an eye axial length and an anterior chamber depth. A distance between particular parts, for example, can be measured properly by utilizing a positional relationship that is set using a standard portion.

The computation control device may acquire combined depth information by combining the first depth information and the second depth information with each other using standard interference signals. The computation control device may combine the first depth information and the second depth information with each other so that positions, in the depth direction, of standard interference signals of light beams coming from the same standard portion coincide with each other (see FIG. 2). The computation control device may combine the first depth information and the second depth information with each other so that the distance between standard interference signals of light beams coming from different standard portions corresponds to a known distance between standard portions (see FIG. 4).

The computation control device may eliminate standard interference signals contained in depth information by signal processing. For example, the computation control device eliminates standard interference signals contained in combined depth information after generating it.

A plurality of pieces of depth information with different optical path length differences may be acquired in such a manner that the optical member that is moved for varying the optical path length is either stopped at a prescribed position or moved (i.e., each piece of depth information is acquired upon arrival of prescribed timing).

<A Plurality of Reference Optical Paths>

The reference optical path may be provided with a first reference optical path (e.g., first reference optical system 300a) and a second reference optical path (e.g., second reference optical system 300b) which is longer than the first reference optical path. For example, the optical path length of the first reference optical path is set so as to be suitable for acquisition of depth information of the cornea and that of the second reference optical path is set so as to be suitable for acquisition of depth information of at least one of the crystalline lens and the fundus.

The computation control device may acquire, as first depth information, depth information that contains a first interference signal of reference light coming from the first reference optical path and measurement light coming from a first part. The computation control device may acquire, as second depth information, depth information that contains a second interference signal of reference light coming from the second reference optical path and measurement light coming from a second part.

The standard optical system 200 may be equipped with a first standard portion for formation of a standard interference signal in a first interference signal and a second standard portion for formation of a standard interference signal in a second interference signal. The optical path length difference varying unit may vary the optical path length difference by varying the optical path length of the second reference optical path. In this manner, the measurement region can be varied from a region including the crystalline lens to a region including the fundus.

In this case, since an interference signal from the first part and an interference signal from the second part can be detected simultaneously, the apparatus 1 is resistant to positional deviations that occur during a measurement and hence high measurement accuracy, for example, is secured.

Part of the standard optical system 200 may be used as a reference optical path. For example, a configuration is possible in which a particular standard portion (e.g., reflection portion 206a) is set higher in reflectivity than the other standard portions and light (reference light) coming from the particular standard portion interferes with measurement light coming from the cornea. In this case, a standard portion having a high reflectivity is used as the first reference path.

<Generation of Tomographic Images>

Where tomographic images are generated by controlling the scanning unit, the computation control device may generate a first tomographic image based on pieces of first depth information acquired at respective scanning positions and generate a second tomographic image based on pieces of second depth information acquired at respective scanning positions.

The computation control device may generate a synthesized tomographic image by combining the first tomographic image and the second tomographic image based on standard interference signals. The computation control device may delete the standard interference signals contained in the synthesized tomographic image after generating it.

The computation control device may detect positions of a first part and a second part in the synthesized tomographic image and determine a distance between the first part and the second part in the eye E based on the detected positions of the first part and the second part.

<Acquisition of Three or More Pieces of Depth Information>

The optical path length difference varying unit may be such as to be able to set at least three different optical path length differences (see FIGS. 2 and 4). The standard optical system 200 may be equipped with a plurality of standard portions according to the at least three optical path length differences produced by the optical path length difference varying unit.

The computation control device may set a positional relationship between the above-mentioned first depth information and third depth information using corresponding standard reference signals as standards. The third depth information may be acquired with a different optical path length difference than the first depth information is, and contain a third interference signal of measurement light coming from a third part of the eye E and reference light. The computation control device may set a positional relationship between the above-mentioned second depth information and third depth information using corresponding standard reference signals as standards.

The computation control device may combine the first depth information, the second depth information, and the third depth information continuously in the depth direction.

<Others>

The ophthalmologic apparatus 1 may perform full-range processing (mirror image elimination processing).

Specific Embodiment 1

As shown in FIGS. 1 and 2, an ophthalmologic apparatus 1 according to a first specific embodiment is an optical coherence tomography (OCT) apparatus. The OCT apparatus according to the first specific embodiment is based on swept source OCT (SS-OCT), for example, and includes the variable wavelength light source 102, the interference optical system (OCT optical system) 100, and the computation control device (control unit) 70. The ophthalmologic apparatus 1 is also equipped with the memory 72, the display unit 75, a front image observation system (not shown), and a fixation target projection system (not shown). The computation control device (hereinafter referred to as a control unit) 70 is connected to the variable wavelength light source 102, the interference optical system 100, the memory 72, and the display unit 75.

Measurement light is introduced to the eye E by the guide optical system 150 of the interference optical system 100. The interference optical system 100 introduces reference light to the reference optical system 300. The interference optical system 100 causes the detector (photodetecting device) 120 to detect interference signal light of interference between measurement light reflected from the eye E and reference light. The ophthalmologic apparatus 1 according to this embodiment is also equipped with the standard optical system 200 (described later in detail). The interference optical system 100 is installed in a body (apparatus body; not shown), and is aligned with the eye E by moving the body three-dimensionally with respect to the eye E by means of a known alignment moving mechanism using a manipulation member such as a joystick.

The interference optical system 100 is of the SS-OCT type, and the light source 102 is a variable wavelength light source (wavelength-scanning light source) in which the wavelength of exit light is varied in time at high speed. For example, the light source 102 is composed of a laser medium, a resonator, and a wavelength selection filter. Examples of the wavelength selection filter are a combination of a diffraction grating and a polygon mirror and a filter using a Fabry-Pérot etalon.

The coupler (splitter, optical splitter) 104 divides light that is emitted from the light source 102 into light beams to travel along the measurement optical path and the reference optical path, respectively. A circulator 103 guides light coming from the coupler 104 to an optical fiber 105, and guides light coming from the optical fiber 105 to an optical fiber 119. The circulator 103 may be a coupler.

A coupler (splitter) 130 divides light (measurement light) coming from the optical fiber 105 into light beams to travel along the optical path of the guide optical system 150 and the optical path of the standard optical system 200. That is, the measurement optical path has the guide optical system 150 and the standard optical system 200. The coupler (splitter) 130 may be a beam splitter.

<Guide Optical System)

The guide optical system 150 is provided to guide measurement light to the eye E. For example, an optical fiber 152, a collimator lens 154, an optical scanner 156, and an objective lens system 158 are arranged in this order in the guide optical system 150.

Measurement light travels through the optical fiber 152 and is then converted by the collimator lens 154 into a parallel beam, which goes toward the optical scanner 156. After passing through the optical scanner 156, the light shines on the eye E via the objective lens system 158. The measurement light shines on both of the anterior chamber and the fundus and is scattered and reflected by the tissues there.

The optical scanner 156 scans the eye E with measurement light in the X and Y directions (lateral directions). The optical scanner 156 is composed of, for example, two galvanometer mirrors whose reflection angles are adjusted as desired by drive mechanisms. The fundus is scanned in desired directions with a light beam emitted from the light source 102 whose reflection (traveling) direction is thus varied. The optical scanner 156 is composed of reflection mirrors (galvanometer mirrors, polygon mirrors, or resonant scanners), acousto-optical devices (AOMs) that vary the light traveling (defection) direction, or the like.

Scattering light (reflected light) that is output from the eye E as a result of the incidence of the measurement light reaches a coupler 350 via the objective lens system 158, the optical scanner 156, the collimator lens 154, the members from the optical fiber 152 to the circulator 103, and the optical fiber 119. The scattering light is combined with reference light by the coupler 350 and thereby interferes with it.

<Standard Optical System>

In the first specific embodiment, the standard optical system 200 is provided to generate a standard signal to be used for combining a plurality of pieces of depth information together. The standard optical system 200 may be equipped with a reflection optical member 204. For example, a collimator lens 202 and the reflection optical member 204 are arranged in order in the standard optical system 200. The reflection optical member 204 is equipped with reflection portions 206a-206e which are arranged in the optical axis direction.

For example, the reflection optical member 204 is formed in such a manner that light transmission members (e.g., glass members or plastic members) 204a-204d are bonded to each other in the optical axis direction. The reflection optical member 204 may be formed by arranging light reflection members capable of transmitting part of incident light (e.g., cellophane members or filters) at respective standard positions (first to fourth positions).

In this case, for example, reflected light is produced at the interface between light reflection members joined to each other that have different reflectivities. Alternatively, reflected light may be produced by a reflective coating. When obtaining the reflection at the junction, a defect in the joint between the bonding agent and the light transmitting member may be utilized.

The first surface of the first light transmission member 204a serves as the first reflection portion 206a, the joining surface between the second surface of the first light transmission member 204a and first surface of the second light transmission member 204b serves as the second reflection portion 206b, the joining surface between the second surface of the second light transmission member 204b and first surface of the third light transmission member 204c serves as the third reflection portion 206c, the joining surface between the second surface of the third light transmission member 204c and first surface of the fourth light transmission member 204d serves as the fourth reflection portion 206d, and the second surface of the fourth light transmission member 204d serves as the fifth reflection portion 206e.

Light coming from the collimator lens 202 is reflected by each of the reflection portions 206a-206e, and resulting reflected light beams return to the collimator lens 202 and the coupler 130. The reflected light beams reflected from the respective reflection portions 206a-206e reach the coupler 350 following the same route as light coming from the guide optical system 150. The reflected light beams reflected from the reflection portions 206a-206e are combined with reference light by the coupler 350 and thereby interferes with it.

The interval Z1 between the reflection portions 206a-206e is set shorter than a measurement range Z2, in the Z direction, of the ophthalmologic apparatus 1 (see FIG. 3). The measurement range Z2 in the Z direction is calculated in advance as a measurement distance from a position (zero delay position) where the optical path length difference between measurement light and reference light becomes zero.

Where full-range processing (mirror image elimination processing) is performed, the measurement range Z2 in the Z direction may be an addition distance of measurement ranges on the positive side and the negative side, respectively, of the zero delay position.

<Reference Optical System>

The reference optical system 300 generates reference light to be combined with reflected light that is generated by reflection of measurement light by the eye E. The reference optical system 300 may be of either the Michelson type or the Mach-Zehnder type.

The reference optical system 300 may be a reflection optical system, in which case light coming from the coupler 104 is reflected by the reflection optical system and thereby introduced to the detector 120. Alternatively, the reference optical system 300 may be a transmission optical system, in which case light coming from the coupler 104 is guided to the detector 120 without making a return travel.

In the apparatus 1, to adjust the optical path length difference between measurement light and reference light, at least part of the optical members 310 which is provided in the interference optical system 100 are moved in the optical axis direction. The drive unit 320 is provided to move (part of) the optical members 310.

For example, the reference optical system 300 has a structure for adjusting the optical path length difference between measurement light and reference light by moving (part of) the optical members 310 provided in the reference optical path.

More specifically, for example, the reference optical system 300 is equipped with a circulator 106, an optical fiber 107, a collimator lens 305, and the optical members 310. The circulator 106 guides light coming from the coupler 104 to the optical fiber 107 and guides light coming from the optical fiber 107 to an optical fiber 109. The circulator 106 may be a coupler.

Reference light coming from the optical fiber 107 is collimated by the collimator lens 305 and then reflected by the optical members 310. Light reflected from each optical member 310 reaches the coupler 350 via the collimator lens 305, the optical fiber 107, the circulator 106, and the optical fiber 109. The reference light is combined with light coming from the measurement optical path by the coupler 350 and thereby interferes with it.

<Photodetector>

The detector 120 is provided to detect interference between light coming from the measurement optical path and light coming from the reference optical path. The detector 120 may perform balanced detection. In this case, the detector 120 is provided with a plurality of photodetecting devices and produces a difference between an interference signal from a first photodetecting device and an interference signal from a second photodetecting device and thereby reduces influences of unnecessary noise contained in the interference signals. Each photodetecting device is a point sensor having only one photodetecting portion, such as an avalanche photodiode.

<Acquisition of Depth Information>

As the wavelength of exit light is varied by the light source 102, corresponding interference signal light is received by the detector 120 and detected by it as a spectral signal. The control unit 70 processes (Fourier-analyzes) the spectral signal detected by the detector 120 and thereby obtains depth information of the eye E.

A spectral signal (spectral data) may be rewritten to a function of the wavelength λ and then converted into a function (k) with regular wave number intervals (wave number $k=2\pi/\lambda$). Alternatively, a function (k) with regular wave number intervals may be obtained from the first (k-clock technique). The control unit 70 may acquire a reflectance distribution in a depth (Z) region by Fourier-transforming a spectral signal in the wave number k space.

Fourier-transformed information may be expressed as a signal including a real part and an imaginary part in the Z space. The control unit 70 may acquire an A-scan signal (signal intensity values in the depth direction) by calculating absolute values of a real part and an imaginary part of a signal in the Z space.

<Control System>

The control unit 70 may be equipped with a CPU (processor), a RAM, and a ROM (see FIG. 1). For example, the CPU of the control unit 70 controls the ophthalmologic apparatus 1. The RAM stores various kinds of information temporarily. The ROM is stored with various kinds of programs, initial values, etc. for control of the operation of the ophthalmologic apparatus 1.

The nonvolatile memory (hereafter abbreviated as a memory) 72, a manipulation unit 74, the display unit 75, etc. may be electrically connected to the control unit 70. The memory 72 may use a nonvolatile storage medium capable of holding storage contents even after a power shutoff, such as a hard disk drive, a flash memory, and a USB memory which can be attached to the ophthalmologic apparatus 1 in a detachable manner. The memory 72 may be stored with control programs for controlling the ophthalmologic apparatus 1 in acquiring depth information and taking tomographic images. The memory 72 may be stored with various kinds of information relating to imaging such as a measurement result of an eye axial length and tomographic images taken. Various kinds of manipulation instructions of an operator may be input to the manipulation unit 74. For example, the manipulation unit 74 may be used for setting of scanning positions and measurement mode switching.

<Operation of Apparatus>

How the ophthalmologic apparatus 1 having the above configuration operates will be described below. First, measurement of an eye axial length will be described. To measure an eye axial length, driving of the optical scanner 156 is suspended. In this state, for example, the deflection angles of the optical scanner 156 may be set so that the visual axis of the eye E and the principal ray of a measurement light beam coincide with each other.

An operator makes alignment adjustments in the X, Y, and Z directions by moving the apparatus body incorporating the interference optical system 100 with respect to the eye E. For example, an anterior chamber image taken by an anterior chamber observation camera (not shown) is displayed on the display unit 75 and the operator makes alignment adjustments using the anterior chamber image.

<Acquisition of and Combining Depth Information>

The control unit 70 acquires pieces of depth information at a plurality of positions by varying the optical path length of reference light by controlling the driving of the drive unit 320. The optical members 310 is moved in the optical axis direction being driven by the drive unit 320, as a result of which the measurement region of the eye E is varied.

Since the apparatus 1 according to this specific embodiment is based on Fourier-domain OCT, depth information corresponding to a measurement range Z1, for example, can be acquired in a state that the optical member 310 is located at a certain position (see FIG. 3). Thus, first depth information Z10 corresponding to the measurement range Z1 can be acquired in a state that the optical member 310 is located at a first position 330a. Likewise, second depth information Z20, third depth information Z30, and fourth depth information Z40 corresponding to the measurement range Z1 can be acquired in states that the optical member 310 is located at a second position 330b, a third position 330c, and a fourth position 330d, respectively.

As a result, the first depth information Z10 contains an interference signal corresponding to the anterior chamber of the eye E, an interference signal 210a corresponding to the first reflection portion 206a, and an interference signal 210b corresponding to the second reflection portion 206b.

In this specific embodiment, the interference signal corresponding to the anterior chamber includes an interference signal AC corresponding to the cornea front surface, an interference signal corresponding to the cornea rear surface (not shown), an interference signal corresponding to the crystalline lens front surface (not shown), etc. Naturally, the invention is not limited to the case that these interference signals are acquired; only part of these interference signals may be detected and an interference signal corresponding to an area of opacity of the crystalline lens of an eye with a cataract may be detected.

An interference signal 210b corresponding to the second reflection portion 206b and an interference signal 210c corresponding to the third reflection portion 206c are detected as the second depth information Z20. An interference signal 210c corresponding to the third reflection portion 206c and an interference signal 210d corresponding to the fourth reflection portion 206d are detected as the third depth information Z30. An interference signal 210d corresponding to the fourth reflection portion 206d and an interference signal 210e corresponding to the fifth reflection portion 206e are detected as the fourth depth information Z40.

The position where an interference signal corresponding to the fundus of the eye E is acquired depends on its axial length. In the example of FIG. 3, an interference signal corresponding to the fundus is detected when the optical member 310 is located at the fourth position 330d. In this specific embodiment, the interference signal corresponding to the fundus includes an interference signal AR corresponding to the retina front surface (not shown) and an interference signal PR corresponding to the retina rear surface. Naturally, the invention is not limited to the case that these interference signals are acquired; only one of these interference signals may be detected and an interference signal corresponding to a choroid layer may be detected.

For example, as described above, the movement interval of the optical member 310 is set so that the measurement regions of pieces of depth information acquired at adjoining positions have an overlap and interference signals corresponding to the same reflection portion are acquired in the overlap region.

<Combining of Pieces of Depth Information>

Pieces of depth information that are acquired at positions corresponding to different optical path lengths of reference light are combined together using, as standards, standard signals generated by the standard optical system 200. Interference signals 210a-210e corresponding to the respective reflection portions 206a-206e are used as standard interference signals (hereinafter referred to as standard signals) to be used in combining pieces of depth information together.

The control unit 70 processes depth information acquired at each position and thereby extracts interference signals corresponding to respective reflection portions. Since the intensities of interference signals corresponding to the respective reflection portions 206a-206e are known, the control unit 70 can extract signals (standard signals) corresponding to the reflection portions 206a-206e by, for example, judging whether or not individual luminance signals of the pieces of depth information exceed threshold values that are set for obtaining interference signals corresponding to the reflection portions 206a-206e.

FIG. 3 shows an example manner of combining pieces of depth information together. The control unit 70 combines pieces of depth information together in such a manner that signals corresponding to the same reflection portion coincide with each other in the depth direction. In this manner, consecutive pieces of depth information containing interference signals corresponding to the anterior chamber to the fundus are acquired.

More specifically, the control unit 70 combines first depth information Z10 and second depth information Z20 with each other so that an interference signal 210b contained in the first depth information Z10 and an interference signal 210b contained in the second depth information Z20 coincide with each other. Likewise, an interference signal 210c is used in combining the second depth information Z20 and third depth information Z30, an interference signal 210d is used in combining the third depth information Z30 and fourth depth information Z40, and an interference signal 210e is used in combining the fourth depth information Z40 and fifth depth information Z50.

In causing signals corresponding to the same reflection portion to coincide with each other in the depth direction the control unit 70 may make position adjustments so that peak positions, corresponding to the same reflection portion, in, for example, the first depth information Z10 and the second depth information Z20 coincide with each other. As for combining for an overlap portion between two pieces of depth information, one of the two pieces of depth information may be employed. Alternatively, an average of the two pieces of depth information may be calculated.

The control unit 70 measures an axial length of the subject eye E based on combined depth information ZS that has been produced in the above-described manner. More specifically, an eye axial length is determined based on pieces of position information of the interference signals AC and PR that are contained in the combined depth information ZS. The control unit 70 displays a measurement result on the display unit 75.

In this manner, an axial length of an eye can be acquired by a simple configuration that is based on Fourier-domain OCT, for example. Furthermore, since the standard optical system 200 having a known optical arrangement is used, positional relationships between difference pieces of depth information can be determined accurately and tissue between particular parts can be measured properly.

<Acquisition of Tomographic Images>

Tomographic images of the eye E may be generated by scanning it with measurement light. More specifically, the control unit 70 controls the driving of the optical scanner 156 to scan the eye E with measurement light in a lateral direction. The control unit 70 may form a synthesized tomographic image by arranging, in order, sets of pieces of combined depth information ZS acquired at respective scanning positions. The control unit 70 displays the synthesized tomographic image on the display unit 75. The synthesized tomographic image contains tomographic images of the anterior chamber and the fundus and thus enables observation of the entire eye E. The synthesized tomographic image may be stored in the memory 72.

The objective lens system 158 may be configured so that the optical scanner 156 and the pupil portion of the eye E are in a conjugate relationship, in which case a measurement beam is rotated about the pupil. The objective lens system 158 may be an image-side telecentric system. In this case, a scanning measurement beam of the optical scanner 156 is kept parallel with the optical axis of the objective lens system 158 irrespective of the scanning position.

With the above-described simple configuration, tomographic images can be generated so as to cover a wide range of the eye E in the optical axis direction (e.g., including a range from the entire eye E from the cornea to the fundus). The control unit 70 may measure an eye axial length by processing a synthesized tomographic image.

Specific Embodiment 2

FIG. 4 shows the configuration of an ophthalmologic apparatus 1 according to a second specific embodiment. In the following description of the second specific embodiment, constituent elements having corresponding ones that function or work in the same manners are given the same reference symbols as the latter and specific descriptions therefor will be omitted.

In the second specific embodiment, the reference optical system 300 has a plurality of optical paths. A first reference optical system 300a is provided to acquire interference signals corresponding to the cornea. A second reference optical system 300b is provided to acquire interference signals corresponding to the crystalline lens or fundus. The optical path length of the second reference optical system 300b is set longer than that of the first reference optical system 300a. When alignment work is completed, the optical path length of the first reference optical system 300a is fixed so that the cornea is included in an interference signal detectable range (i.e., a range in which a tomographic image can be taken). The specific configuration of each of the first reference optical system 300a and the second reference optical system 300b can be modified in various manners like the reference optical system 300 of the first specific embodiment.

More specifically, for example, the reference optical system 300 is equipped with a beam splitter 360 for dividing reference light into first reference light and second reference light. The beam splitter 360 is a polarizing beam splitter, for example. However, this specific embodiment is not limited to this case and the beam splitter 360 may be a coupler. It is preferable that a light shield unit be disposed in each of the first reference optical path and the second reference optical path so as to be inserted into and removed from it so that a measurement using the first reference optical path and a measurement using the second reference optical path can be performed selectively. In this case, the optical path switching may be made frame by frame. In this case, the optical path switching may be made by an optical switch. Where the optical switch is used, for example, the reference light optical path can be switched selectively between the first reference optical path and the second reference optical path, whereby a cornea tomographic image and a lens tomographic image (or fundus tomographic image) are generated alternately. For example, an optical member 310a (e.g., reference mirror) is disposed fixedly in the first optical system 300a.

For example, an optical member 310b (e.g., reference mirror) that is moved to adjust the optical path length difference between measurement light and reference light is disposed in the second reference optical system 300b. A drive unit 320b is provided to move the optical member 310b.

Reference light coming from the optical fiber 107 is collimated by the collimator lens 305 and then divided into first reference light and second reference light by the beam splitter 360. The first reference light is reflected by a mirror 303 and the optical member 310a and then reaches the coupler 350 via the members from the mirror 303 to the optical fiber 109. The first reference light is combined with cornea reflected light coming from the measurement optical path by the coupler 350 and thereby interferes with it.

Second reference light is reflected by the optical member 310b and then reaches the coupler 350 via the members from the beam splitter 360 to the optical fiber 109. The second reference light is combined with reflected light (e.g., lens reflected light or fundus reflected light) coming from the measurement optical path by the coupler 350 and thereby interferes with it.

In the standard optical system 200 of the second specific embodiment, the reflection optical member 204 is equipped with reflection portions 206a-206d which are arranged in the optical axis direction. For example, the reflection optical member 204 is formed in such a manner that light transmission members (e.g., glass members or plastic members) 204a-204d are bonded to each other in the optical axis direction. In the second specific embodiment, the interval Z1 between the reflection portions 206a-206d is set longer than a measurement range Z2 of the ophthalmologic apparatus 1 in the Z direction.

How the apparatus 1 according to the second specific embodiment operates will be described below. In the second specific embodiment, typically, tomographic images are generated by driving the optical scanner 156 and an eye axial length is measured based on the generated tomographic images. However, the second specific embodiment is not limited to this case; as in the first specific embodiment, an eye axial length may be measured in a state that the driving of the optical scanner 156 is suspended.

In the second specific embodiment, since the optical member 310a is fixed at a first position 330a, first depth information Z10 corresponding to the measurement range Z1 (including a cornea region) can be acquired steadily. As a result, the first depth information Z10 contains at least an interference signal corresponding to the cornea of the eye E and an interference signal 210a corresponding to the first reflection portion 206a.

The control unit 70 acquires pieces of depth information Z20-Z40 at a plurality of positions (second to fourth positions) by varying the optical path length of reference light by controlling the driving of the drive unit 320b. The second depth information Z20, third depth information Z30, and fourth depth information Z40 are acquired when the optical member 310b is located at a second position 330b, a third position 330c, and a fourth position 330d, respectively. The second depth information Z20 contains at least an interference signal corresponding to the crystalline lens of the eye E. The first depth information Z10 is acquired when the first reference optical path is selected temporarily by a reference optical path selecting operation in acquiring the pieces of depth information Z20-Z40. As a result, the first depth information Z10 is acquired approximately simultaneously with the other pieces of depth information.

The position at which an interference signal corresponding to the fundus of the eye E is acquired depends on its axial length. FIG. 5 shows an example that an interference signal corresponding to the fundus is acquired when the optical member 310b is located at the forth position 330d.

For example, as described above, the movement interval of the optical member 310 is set so that the interference signal of reflection portions are detected at end portions of pieces of depth information acquired at adjoining positions. In the example of FIG. 5, the movement interval is set so that interference signals of the respective reflection portions occur alternately on the front side and the rear side of the 0-delay position.

FIG. 5 shows an example manner of combining pieces of depth information together. The control unit 70 combines together pieces of depth information that are acquired at positions corresponding to different optical path lengths of reference light using, as standards, standard signals generated by the standard optical system 200. Interference signals 210a-210d corresponding to the respective reflection portions 206a-206d are used as standard signals to be used in combining pieces of depth information together. As for combining for an overlap portion between two pieces of depth information, one of the two pieces of depth information may be employed. Alternatively, an average of the two pieces of depth information may be calculated.

The control unit 70 combines pieces of depth information together so that the distance between standard signals contained in pieces of depth information corresponds to the distance between the corresponding reflection portions. The control unit 70 combines first depth information Z10 and second depth information Z20 together so that the distance between an interference signal 210a contained in the first depth information Z10 and an interference signal 210b contained in the second depth information Z20 corresponds to the known distance between the reflection portions 206a and 206b. As a result, combined depth information ZS1 containing interference signals corresponding to the cornea and the anterior chamber is obtained.

The control unit 70 combines the first depth information Z10 and third depth information Z30 together so that the distance between the interference signal 210a contained in the first depth information Z10 and an interference signal 210c contained in the third depth information Z30 corresponds to the known distance between the reflection portions 206a and 206c. As a result, combined depth information ZS2 containing interference signals corresponding to the cornea and the fundus is obtained.

The control unit 70 combines the first depth information Z10 and fourth depth information Z40 together so that the distance between the interference signal 210a contained in the first depth information Z10 and an interference signal 210d contained in the fourth depth information Z40 corresponds to the known distance between the reflection portions 206a and 206d. As a result, combined depth information ZS3 containing interference signals corresponding to the cornea and the fundus is obtained.

The control unit 70 measures an axial length of the eye E based on the pieces of combined depth information ZS1-ZS3 that have been produced in the above-described manner. More specifically, an eye axial length is determined based on pieces of position information of interference signals AC and PR that are contained in the pieces of combined depth information ZS1-ZS3. The control unit 70 displays a measurement result on the display unit 75.

More specifically, the control unit 70 determines combined depth information that contains both interference signals corresponding to the cornea and the fundus from the pieces of combined depth information ZS1-ZS3. The control unit 70 determines an eye axial length based on pieces of position information of interference signals AC and PR that are contained in the determined combined depth information.

The control unit 70 may combine the combined depth information ZS1 with each of the third depth information Z30 and fourth depth information Z40. In this case, the control unit 70 may perform combining processing so that the distance between a standard signal (e.g., interference signal 210*a*) contained in the combined depth information ZS1 and a standard signal contained in the third depth information Z30 or the fourth depth information Z40 corresponds to the known distance between the reflection portions (e.g., reflection portions 206*a* and 206*c*). In this manner, consecutive pieces of depth information containing interference signals corresponding to the anterior chamber to the fundus are acquired.

With the above-described configuration, since a peak corresponding to the cornea is detected steadily, dimensions of the eye E can be measured accurately even if it moves during the measurement.

What is claimed is:

1. An ophthalmologic apparatus comprising:
   an interference optical system including:
   a light source to emit light;
   a measurement optical path configured to guide, to an eye, measurement light which is generated based on the light emitted from the light source;
   a reference optical path configured to generate reference light which is generated based on the light emitted from the light source;
   a standard optical system including an optical member, the standard optical system being configured to generate a standard interference signal which is an optical interference signal from the optical member; and
   a detector configured to generate a detection signal containing an interference signal of the measurement light guided to the eye via the measurement optical path, the reference light coming from the reference optical path, and the standard interference signal; and
   a processor configured to:
   acquire first depth information including a first interference signal of the measurement light coming from a first part of the eye and the reference light by processing the detection signal received from the detector, an optical path length difference between the measurement optical path and the reference optical path is a first value;
   acquire second depth information including a second interference signal of the measurement light coming from the second part of the eye and the reference light by processing the detection signal received from the detector where the optical path length difference is a second value different from the first value;
   set a positional relationship between the first depth information and the second depth information based on the standard interference signal detected by the detector; and
   generate synthesized depth information by synthesizing the first depth information and the second depth information using the standard interference signals.

2. The ophthalmologic apparatus according to claim 1, wherein the processor is configured to:
   detect a position of the first part based on the first depth information;
   detect a position of the second part based on the second depth information; and
   determine a distance between the first part and the second part in the eye based on the detected position of the first part, the detected position of the second part and the set positional relationship.

3. The ophthalmologic apparatus according to claim 1, wherein the processor is configured to detect a position of the first part and a position of the second part in the synthesized depth information and determine a distance between the first part and the second part in the eye based on the detected position of the first part and the detected position of the second part.

4. The ophthalmologic apparatus according to claim 1, wherein
   the reference optical path includes a first reference optical path and a second reference optical path which is longer than the first reference optical path;
   the processor is configured to:
   acquire the first depth information including a first interference signal of the reference light coming from the first reference optical path and the measurement light coming from the first part of the eye;
   acquire the second depth information including a second interference signal of the reference light coming from the second reference optical path and the measurement light coming from the second part of the eye; and
   set a positional relationship between the first depth information and the second depth information based on the standard interference signal.

5. The ophthalmologic apparatus according to claim 1, wherein
   the measurement optical path includes a scanner configured to scan the eye with the measurement light, and
   the processor is configured to generate a first tomographic image based on the first depth information acquired at respective scanning positions scanned by the scanner and generate a second tomographic image based on the second depth information acquired at respective scanning positions scanned by the scanner.

6. The ophthalmologic apparatus according to claim 5, wherein the processor is configured to generate a synthesized tomographic image by synthesizing the first tomographic image and the second tomographic image using the standard interference signal.

7. The ophthalmologic apparatus according to claim 6, wherein the processor is configured to detect a position of the first part of the eye in the synthesized tomographic image and a position of the second part of the eye in the synthesized tomographic image and determine a distance between the first part and the second part in the eye based on the detected position of the first part and the detected position of the second part.

8. The ophthalmologic apparatus according to claim 1, further comprising:
   an actuator configured to set at least three different optical path length differences; and a plurality of optical members disposed corresponding to the at least three optical path length differences, respectively, wherein the processor is configured to:

acquire third depth information including a third interference signal of the measurement light coming from a third part of the eye and the reference light by processing the detection signal received from the detector where the optical path length difference is a third value different from the first value and the second value; and set a positional relationship between the first depth information and third depth information based on the standard interference signal which is the interference signal of the lights coming from the optical members corresponding to the first part of the eye and the third part of the eye.

9. The ophthalmologic apparatus according to claim 1, further comprising:

an actuator configured to set at least three different optical path length differences;

a plurality of optical members disposed corresponding to the at least three optical path length differences, respectively; and wherein the processor is configured to:

acquire third depth information including a third interference signal of the measurement light coming from a third part of the eye and the reference light by processing the detection signal received from the detector where the optical path length difference is a third value different from the first value and the second value; and set a positional relationship between the second depth information and third depth information based on the standard interference signal which is the interference signal of the lights coming from the optical members corresponding to the second part of the eye and the third part of the eye.

10. An ophthalmologic apparatus comprising:

an interference optical system including:

a light source to emit light;

a measurement optical path configured to guide, to an eye, measurement light which is generated based on the light emitted from the light source;

a reference optical path configured to generate reference light which is generated based on the light emitted from the light source;

a standard optical system including an optical member, the standard optical system being configured to generate a standard interference signal which is an optical interference signal from the optical member; and a detector configured to generate a detection signal containing an interference signal of the measurement light guided to the eye via the measurement optical path, the reference light coming from the reference optical path, and the standard interference signal; and a processor configured to:

acquire first depth information including a first interference signal of the measurement light coming from a first part of the eye and the reference light by processing the detection signal received from the detector, an optical path length difference between the measurement optical path and the reference optical path is a first value;

acquire second depth information including a second interference signal of the measurement light coming from the second part of the eye and the reference light by processing the detection signal received from the detector where the optical path length difference is a second value different from the first value;

set a positional relationship between the first depth information and the second depth information based on the standard interference signal detected by the detector;

detect a position of the first part based on the first depth information;

detect a position of the second part based on the second depth information; and determine a distance between the first part and the second part in the eye based on the detected position of the first part, the detected position of the second part and the set positional relationship.

11. An ophthalmologic apparatus comprising:

an interference optical system including:

a light source to emit light;

a measurement optical path configured to guide, to an eye, measurement light which is generated based on the light emitted from the light source;

a reference optical path configured to generate reference light which is generated based on the light emitted from the light source, the reference optical path including a first reference optical path and a second reference optical path which is longer than the first reference optical path;

a standard optical system including an optical member, the standard optical system being configured to generate a standard interference signal which is an optical interference signal from the optical member; and a detector configured to generate a detection signal containing an interference signal of the measurement light guided to the eye via the measurement optical path, the reference light coming from the reference optical path, and the standard interference signal; and a processor configured to:

acquire first depth information including a first interference signal of the measurement light coming from a first part of the eye and the reference light by processing the detection signal received from the detector, an optical path length difference between the measurement optical path and the reference optical path is a first value;

acquire second depth information including a second interference signal of the measurement light coming from the second part of the eye and the reference light by processing the detection signal received from the detector where the optical path length difference is a second value different from the first value;

set a positional relationship between the first depth information and the second depth information based on the standard interference signal detected by the detector;

acquire the first depth information including a first interference signal of the reference light coming from the first reference optical path and the measurement light coming from the first part of the eye;

acquire the second depth information including a second interference signal of the reference light coming from the second reference optical path and the measurement light coming from the second part of the eye; and set a positional relationship between the first depth information and the second depth information based on the standard interference signal.

\* \* \* \* \*